United States Patent [19]

Pedersen

[11] 4,167,879
[45] Sep. 18, 1979

[54] METHOD AND APPARATUS FOR EXAMINING A SOLID

[75] Inventor: Norman E. Pedersen, Wilmington, Mass.

[73] Assignee: Panametrics, Inc., Waltham, Mass.

[21] Appl. No.: 913,065

[22] Filed: Jun. 6, 1978

[51] Int. Cl.[2] .......................................... G01N 29/04
[52] U.S. Cl. ........................................ 73/610; 73/620
[58] Field of Search ................ 73/596, 609, 610, 611, 73/612, 618, 620, 624, 625, 627, 628, 632, 641; 340/1 R, 15.5 R

[56] References Cited

U.S. PATENT DOCUMENTS

| 3,108,249 | 10/1963 | Clement | 340/15.5 R |
| 3,228,232 | 1/1966 | Proctor | 73/628 |
| 3,675,472 | 7/1972 | Kay et al. | 73/626 |
| 3,803,598 | 4/1974 | Abernathy et al. | 340/15.5 SC |

Primary Examiner—Stephen A. Kreitman
Attorney, Agent, or Firm—Kenway & Jenney

[57] ABSTRACT

An apparatus and method for examining the structure of and in particular detecting flaws within a solid are disclosed. The transmitting source directs pseudo-random coded, phase modulated, interrogation signals, at a plurality of frequencies, toward the object being examined. At the receiver, the returning interrogation signals, reflected by structure within the solid object, are demodulated, employing a delayed replica of the pseudo-random code, and are thereafter processed to provide, preferably, both the phase and magnitude of the returning signals relative to the transmitted interrogation signals. The delayed replica of the pseudo-random code provided to the receiver is delayed by selected time increments to provide a range gate. Thus, the data provided by the receiver represents the amplitude and phase of returning signals as a function of both transit time and frequency. By maintaining a sufficiently small transmitting beam or field of view, the resolution of the beam can be made quite small; and for each source transducer position, the transit time can be related to a known examination cell of the solid. The preferred method of the invention further comprises forming determinants based upon at least the phase and magnitude signals to provide an analysis of the solid structure. In preferred embodiments, the frequency may be sequentially varied according to a predetermined pattern, or a plurality of frequencies can be directed toward the object simultaneously. In either circuit configuration, switches and narrow band filters may be provided for separating the received returning signals.

28 Claims, 8 Drawing Figures

METHOD AND APPARATUS FOR EXAMINING A SOLID

BACKGROUND OF THE INVENTION

The invention relates generally to a method and apparatus for establishing, examining, or analyzing the structure of a solid, and in particular, to a method and apparatus for detecting flaws in a solid.

Many methods and apparatus exist today for making measurements upon a solid. The solid may be for example a cast iron manufactured part, the human body, or the earth (during, for example, seismic investigations). The prior art methods and apparatus include X-ray examination, ultrasonic examination, visual examination, explosive and destructive techniques. The present invention is directed to improvements in the ultrasonic examination of solids.

The utlrasonic examination of solids is generally considered a well established art. Conventional prior art systems use either a pulse echo technique, which is most common, or a continuous interrogation signal using, for example, a random noise generator. In the pulse echo technique, a short pulse is directed toward the solids being examined and the returning echos are received and recorded. The returning signal data is processed to determine the existence of unwanted flaws or other structural irregularities. This technique unfortunately has a limited average power input to the solid, and, as the shape of the solid to be examined becomes more complex, provides increasingly poor performance. Also a wide band receiver is required which often results in a poor signal to noise ratio.

The continuous signal techniques, provided for example by Proctor, U.S. Pat. No. 3,228,232, provide limited data, and have serious shortcomings as the geometry of the object being examined becomes more complex.

It is therefore an object of the invention to provide an apparatus and method for examining a solid which are capable of interrogating a solid of simple or complex shape. Other objects of the invention are a method and apparatus which are reliable, which provide significantly greater information than is available from earlier techniques, and which can be adapted to either real time investigations or to investigations in which later processing is available.

Other objects of the invention include an apparatus and method which is flexible, which provide extremely high detection rates, which has low false alarm rates, and to which statistical estimation techniques can be adapted for increasing both reliability and performance of the apparatus.

SUMMARY OF THE INVENTION

The invention relates to an apparatus and method for examining the structure of a solid. The apparatus, according to the invention, has a transmitting element and a receiving element. The transmitting element features apparatus for repeatedly directing a phase modulated, discrete frequency, interrogation signal at the solid. The interrogation signal has a plurality of time sequential modulated component signals, each component signal being associated with a different discrete frequency. The modulating signal corresponds to a repeatedly generated pseudo-random code in the preferred embodiment. The receiving element is responsive to interrogation signals returning from the solid and, in response to those signals and to the modulating signal delayed according to a predetermined sequence of time durations, generates signals sequentially representing at least one parameter of the return signal, for example, the magnitude and/or phase, corresponding to sequentially selected examination cells within the solid.

In particular, the apparatus according to the invention, features transducer means responsive to electrical input signals for directing the interrogation signal toward the solid and for converting returning interrogation signals from the solid into received electrical signals. The transmitter source provides the electrical input signals and features a code generating element for providing a repeating coded electrical signal output, a frequency selection and generating element for generating electrical continuous wave signals according to a time sequence of selected discrete frequencies, and at least one modulation element for modulating the continuous wave signals with the coded electrical signal output for producing the electrical input signals for the transducer means. The receiving element is responsive to the received electrical signals from the solid as noted above. The receiving element demodulates and range gates the received signals for repeatedly providing electrical output data signals corresponding to selected sequential portions of the received signals relative to the continuous wave carrier signal.

The receiver further features, in one aspect of the invention, at least one demodulation element responsive to a delayed electrical coded signal output and to the received electrical signals for demodulating the received electrical signals and for providing a demodulated received signal output. The receiver further features, in this aspect, at least one element associated with and responsive to each of the demodulated received signals and to a continuous wave reference signal. The reference signal has the same instantaneous frequency as the corresponding continuous wave signal and a selected phase relationship to the corresponding continuous wave signal for generating the electrical output data signals.

In a preferred aspect of the invention the transducer means comprises plural source transducers and plural receiving transducers. In this aspect, the transmitting source has means for simultaneously generating a plurality of continuous wave signals at selected discrete frequencies, separate modulation elements associated with each of the continuous wave signals for modulating the respective continuous wave signal with the selected coded signal, and elements for applying the modulated signal outputs to the separate ones of the source transducers. Correspondingly, the receiving element further has separate demodulator elements responsive to the delayed coded signals for simultaneously demodulating the outputs of the respective receiver transducers. The receiver further has means for filtering the demodulated outputs for providing a plurality of filtered output signals corresponding respectively to the plural continuous wave signals, and elements associated with each filtered signal, and responsive to a corresponding continuous wave reference signal, for generating corresponding output data signals representing at least one of the magnitude and phase of the filtered signal.

Preferably, the phase modulating elements provide modulation of the continuous wave signals in response to a repeating pseudo-random code of a selected length.

The method for analyzing the structure of a solid, according to the invention, features the step of directing interrogation signal energy toward the solid at each of a plurality of interrogation frequencies, the interrogation signal having a plurality of different, discrete frequency, continuous wave signals each modulated by a repeating code signal. The method further features the steps of receiving returning interrogation signals from the solid and providing, from the received returning signals, data output signals, for each discrete frequency, and representing at least one parameter, preferably both the phase and magnitude of the returning signals, as a function of transit time.

In a preferred aspect of the invention, the method further features the steps of generating at least one discriminant value based upon the data output signals and estimating the structure of the solid based upon the at least one discriminant value. Discriminant values of particular interest include the spatial gradient of the phase or the magnitude of the returning signals as a function of frequency; the absolute phase or magnitude of the returning signals, within a selected examination cell of the solid, as a function of frequency; the rate of change of the phase or the magnitude of the returning signals within a selected examination cell of the solid as a function of frequency; or the integral, over the applied frequency range, of the returning signal magnitude for examination cells of the solid.

Preferably, the interrogation frequencies are selected close enough to permit interpolation between data corresponding to adjacent frequencies and therefore the method further features the step of interpolating the phase and signal magnitude values for a selected examination cell of the solid between adjacent interrogation signal frequencies.

In another aspect of the invention, the method features the steps of simultaneously directing interrogation energy at each of a plurality of frequencies into the solid and simultaneously receiving the returning signals at each of a plurality of receiving transducers.

Preferably, the method further includes the steps of generating a repeating pseudo-random code for the code signal, time gate demodulating the returning signals using a delayed replica of the generated pseudo-random code, and selectively varying the time delay of the replica.

DESCRIPTION OF THE DRAWINGS

Other objects, features, and advantages of the invention will appear from the following description of particular embodiments of the invention taken together with the drawings in which.

DESCRIPTION OF PARTICULAR PREFERRED EMBODIMENTS OF THE INVENTION

Figure 1:
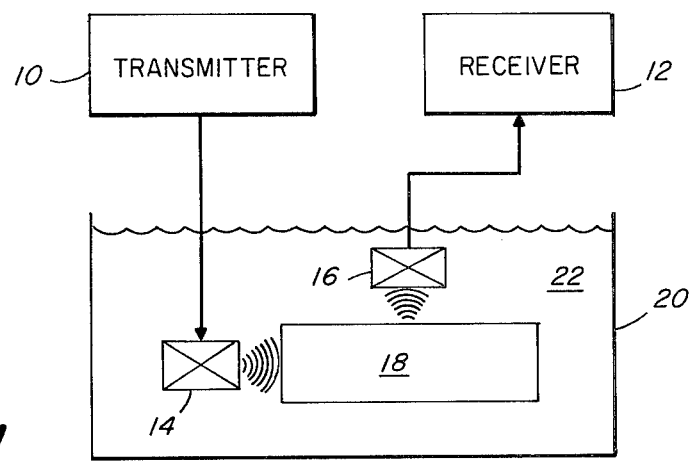
FIG. 1 is a schematic representation of a representative application environment of the invention.

Referring to FIG. 1, the apparatus according to the invention, has a transmitter or transmitting element 10 and a receiver or receiving element 12, which include respectively a transmitting transducer 14 and a receiving transducer 16. The transducers are shown physically separate from elements 10 and 12 respectively. The transmitting transducer 14, the receiving transducer 16 and a solid 18 to be examined are immersed in a tank 20 filled with water 22.

The transmitter 10 provides electrical energy to excite transmitting transducer 14. Transducer 14 provides an interrogation energy output signal directed toward solid 18. The interrogation signal is typically an ultrasonic acoustical wave which, as described in greater detail below, has a plurality of discrete frequency components. The receiving transducer 16 receives returning interrogation energy signals which have been reflected by the structure of the solid. Transducer 16 can be fixed in position relative to the solid 18 or can be translated across the top surface of solid 18 to scan the surface. Preferably both the transmitting and the receiving transducers have a narrow field to provide increased resolution and performance for the apparatus.

As shown, transducers 14 and 16 are separate and distinct from one another. In other embodiments the transducers may form as integral structure. Further, as described below, plural transmitting and/or receiving transducers may be provided, and may be distinct elements or may be integrated physical structures.

The transmitting element 10 according to the invention repeatedly directs a phase modulated, discrete frequency, interrogation signal toward solid 18.

Figure 2:
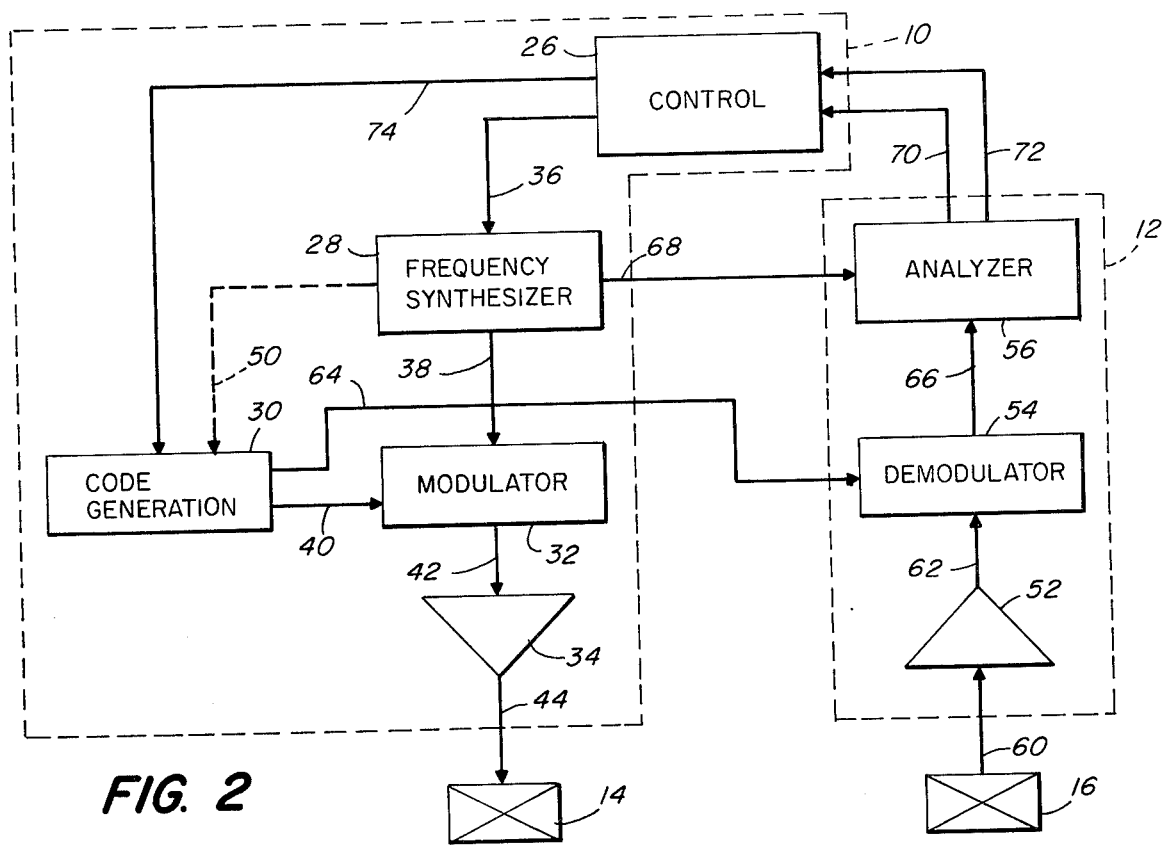
FIG. 2 is an electrical block diagram of a first particular embodiment according to the invention.

Referring to FIG. 2, the transmitter 10 has a control element 26, a frequency synthesizer 28, a code generation element 30, a modulator 32, and an amplifier 34. In this particular embodiment of the invention, the function of control element 26 is conveniently implemented on an appropriately programmed Hewlett-Packard Model HP 9825A computer. The control element in other embodiments of the invention may be a hard-wired device. This is especially true when greater speed is imperative. The control element 26 provides time sequencing to generate, at the output of transducer 14, a time sequence of modulated output signals having different discrete frequencies. Control element 26 also programs code generation element 30 to provide a replica of its output delayed by a selected, varying, time delay. This is described in more detail below.

The frequency synthesizer is preferably a Hewlett-Packard Model 3330B automatic synthesizer which provides, in response to a digital input control signal over lines 36 from control element 26, an output sinusoidal waveform over line 38 having the selected frequency specified by the digital input over lines 36. The sinusoidal output of the frequency synthesizer is applied to modulator 32. Preferably modulator 32 is a double balanced mixer (DBM) as is well known in the art.

The modulating signal over line 40 is a coded signal from code generation element 30. Preferably, the code generation element is a pseudo-random code generator as is also well known in the art. The pseudo-random code generator repeatedly provides a pseudo-random code of selected length having the following random properties: first, in each period of the sequence defining the code word, the number of ones differ from the number of zeros by at most one; second, among the runs of ones and zeros in each code word, one-half of the runs of each kind are of length one, one-fourth are of length two, one-eighth are of length three, etc.; and third, if a period of a sequence is compared, term by term, with any cyclic shift of itself, the number of agreements differ from the number of disagreements by at most one. The modulated output signal over line 42 is preferably applied to the amplifier 34 which may be for example the Model 5050PR manufactured by Panametrics, Inc. of Waltham, Massachusetts. The output of the amplifier over line 44 is applied to the transducing element 14.

The output waveform over line 44 is thus a sinusoidal carrier wave having a frequency which varies discretely over time, and which is phase modulated by a repeating pseudo-random code signal. The pseudo-random code generator 30 provides a code word of length $2^N - 1$ (where N is the number of stages of a code generating shift register), which periodically repeats, and which has the random properties described above. The time required to generate the entire pseudo-random code word, is defined as $T_w$. The bit time of the pseudo-random code, that is, the inverse of the frequency $f_c$, at which code bits are generated, is defined as $T_b = 1/f_c$ (see FIG. 3A). Thus, the pseudo-random code, typically of length 511 bits, 1023 bits, 2047, etc. bits, has a word time $T_w = (2^N - 1)T_b$. (Word lengths less than 511 bits generally do not provide the needed signal to noise ratio for reliable performance of the system, while word lengths greater than 2047 bits are generally difficult to process in real time.)

Figure 3A:
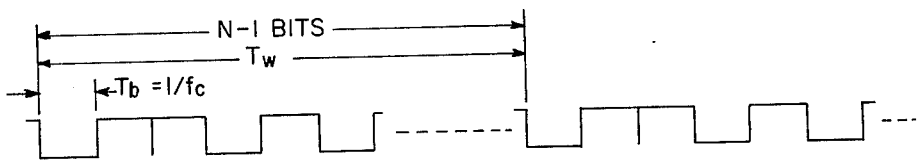
FIGS. 3A, 3B, and 3C are particular waveforms generated in accordance with the operation of the first particular embodiment according to the invention.
Figure 3B:
Figure 3B:
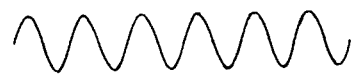

FIG. 3A describes a typical pseudo-random code waveform. This waveform phase modulates the sinusoidal waveform of the frequency synthesizer. FIG. 3B illustrates a typical signal output from frequency synthesizer 38. The resulting output of the modulator 32 over lines 42 (FIG. 3C) has a Fourier transform as shown in FIG. 3D. Referring to FIG. 3D, the spectrum of the output of double balanced mixer 32 has a (sin x/x) envelope within which the spectral lines 46 are contained. The first, and largest lobe of the envelope has a frequency spread between "zero points" equal to $1/T_b$. This corresponds to the code bit repetition rate. The frequency difference between adjacent spectral lines corresponds to $1/T_w$ which relates back to the word length of the repeating pseudo-random code. Importantly, as will be noted later, the spectrum, which is centered around the frequency designated $f_o$, of the sinusoidal input to the modulator from synthesizer 28, does not have a spectral component at the original frequency $f_o$.

Figure 3C:
Figure 3C:
Figure 3D:
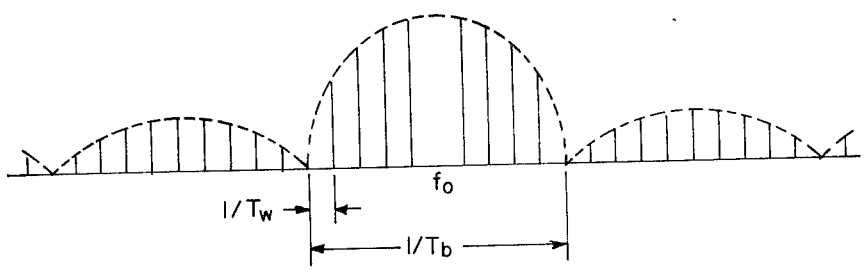
FIG. 3D is the Fourier transform of a typical interrogation signal component according to the invention.

As shown in FIGS. 3A, 3B, 3C, the code generating element is synchronized to frequency synthesizer 38 and the bit rate $1/T_b$ of code generating element 30 not only equals the frequency output of the frequency synthesizer 38, but in addition, code generation element 30 provides transitions at the zero crossing points of the output of synthesizer 28 over lines 38. The code generation element for this particular embodiment may thus be synchronized to the output of the frequency synthesizer as indicated by the dashed line connection 50. In other embodiments of the invention, the code generation need not be synchronized to the frequency synthesizer and may run asynchronously. This should not adversely affect operation of the apparatus and may increase performance of the apparatus by reducing beat frequencies between the various waveforms.

The interrogation signal output thus has a plurality of signal components occurring in time sequence. The $i^{th}$ signal component results from the modulation of a sinusoidal continuous wave signal of frequency $f_i$, $i = 1, 2, \ldots, M$, by a repeating pseudo-random coded signal. In the preferred embodiment the coded signal runs asynchronously with respect to the frequency synthesizer output, and the frequency output of the synthesizer covers a frequency range of 1–10 megahertz. Preferably the frequencies $f_i$ are chosen so that $f_i > f_{i-1}$.

The receiving element 12, referring to FIG. 2, comprises an amplifier 52, a demodulator 54, and an analyzing element 56. The returning interrogation signals are converted by receiving transducer 16 into a received electrical signal over a line 60, and are preferably amplified by amplifier 52 which may be the Panametrics Model 5050PR. The output of amplifier 52 is applied to demodulator 54 over line 62. The demodulator 54 effects demodulation of the returning signal and simultaneously provides a range gating function. Thus, demodulator 54 which may be a double balanced mixer as is well known in the art, receives over lines 64 a delayed version or replica of the output of code generation element 30 which was originally used to modulate the output of synthesizer 28. Thus, the phase modulated returning signal is again phase modulated (or demodulated) by a suitably delayed replica of the same code signal. If the delay corresponds to the round trip transit time from the transmitting transducer to the structural reflecting location and then to the receiving transducer, the output over line 66 corresponds to the original sinusoidal carrier of frequency $f_o$. If other returning signals reflected by other structure of the solid are also present, the demodulated signal has the desired waveform at the original frequency $f_o$ plus unwanted signals at other spectral frequencies. A filter in analyzer 56 will separate the spectral line at $f_o$ from the other unwanted frequencies. By varying the delay of the replica of the pseudo-random code over line 64, range gating is achieved, that is, by varying the delay of the replica selected portions of the solid can be examined. Each selected portion, designated an examination or interrogation cell, corresponds substantially to a volume having a cross section defined by the transmitted beam field of view and a depth substantially equal to one-half the distance traveled by the ultrasonic signal in the solid in a time equal to $T_b$. The position of the selected cell corresponds to a transit time equal to one-half the delay of the code word replica.

In summary, the output of the modulator over line 66, thus has a spectral component at frequency $f_o$ (the frequency of the frequency synthesizer output for the time corresponding to the delay time) representing structural irregularities in a selected cell, and an output signal having a spectrum not including a component of frequency $f_o$ for those returning signals not emanating from the selected cell. By varying the delay time, successive cells of the solid can be interrogated.

The output signal of the modulator over line 66 is provided to the analyzer element 56 which may be, for example, a Hewlett-Packard network analyzer Model 3570A. The analyzer is also provided, over a line 68, with a reference signal corresponding to the output of frequency synthesizer 28 over line 38. The output of the network analyzer 56 over lines 70, 72 in the preferred embodiment, is both the magnitude and phase of the input signal over line 66, at the frequency $f_o$, relative to the frequency synthesizer output. This output data is provided to the control element 26 for storage and processing.

According to the invention, significant advantage can be obtained by interrogating or directing different discrete frequency signals toward the solid and receiving and recording the signals returning therefrom. Thus, the control element 26 cycles the frequency synthesizer through a plurality of discrete frequencies in the range of, for example, 1–10 mhz. and preferably 1–5 mhz. The number of different frequencies may range from 2 to 100 and is preferably between 30 and 100. Thus, the control element 26 provides a sequencing control signal over line 36 to discretely vary the frequency output of synthesizer 28 according to established criteria so that the plurality of discrete sinusoidal output signals are applied to modulator 32. Simultaneously, the control element 26 can further provide over line 74, for each discrete output frequency of the synthesizer 28, the required delay programming to delay the pseudo-random code output over line 64 by selected amounts. Therefore, according to the invention, the apparatus of FIG. 2 directs a continuous stream of energy toward a solid 18 and receives and processes the returning signals to resolve a plurality of amplitude and phase data for each of a plurality of interrogation cells and at each of a plurality of frequencies. The resulting data accumulation is preferably formed into a plurality of discriminants which can be analyzed by a data processing element to identify those cells for which the value of one or more of the discriminants falls outside a predetermined range of values. This procedure identifies structural variations in the solid with high reliability.

The particular discriminants which are useful are, for example, the absolute phase and rate of change of phase within a resolution cell versus frequency; the signal magnitude and the rate of change of signal magnitude within a cell versus frequency; the signal magnitude integrated over the entire frequency range; the inverse Fourier transform of the signals, and the spatial gradient of the phase or the signal magnitude as a function of frequency.

As noted above, the resolution cell has a "depth" which depends upon the bit rate, $f_c$, of the modulating code word. Thus even though the carrier frequency varies, the size of the resolution cell remains constant so long as the bit rate $f_c$ remains constant. Thus the code generation element can advantageously be operated at a fixed bit rate in order to maintain a fixed cell resolution size. Thus, the bit rate of the code generation element should remain constant irrespective of the frequency output of synthesizer 28 and as a result, the bit transitions of the asynchronously operating code generation element will not occur solely at the zero crossing points but will generally also occur, depending upon the selection of bit rate and carrier frequencies, at non-zero crossing points as well.

In another aspect of the invention, to decrease the interrogation time when a large number of frequencies are employed, a plurality of transmitting and receiving transducers may be employed. Thus in a second particular embodiment of the invention, the plural transmitting transducers and the receiving transducers are selectively operated in pairs, that is, one transmitting and one receiving transducer at a time. In this manner physical movement of the transmitting or receiving transducers is eliminated.

In another aspect of the invention, wherein plural receiving and transmitting transducers are employed, the transmitting transducers are operated simultaneously (or in any convenient combination) with different discrete modulated frequencies. In this third particular embodiment, a plurality of modulators are required and a frequency synthesizer (or alternatively plural crystal controlled oscillators) having the capability of providing simultaneously a plurality of sinusoidal output frequencies provides the continuous wave signals to the modulators. At the receiving element, separate demodulators, one connected to each of the active receiving transducers, and a corresponding plurality of crystal filters are employed to separate the information bearing desired signals from the noise as described in more detail below.

Figure 4:
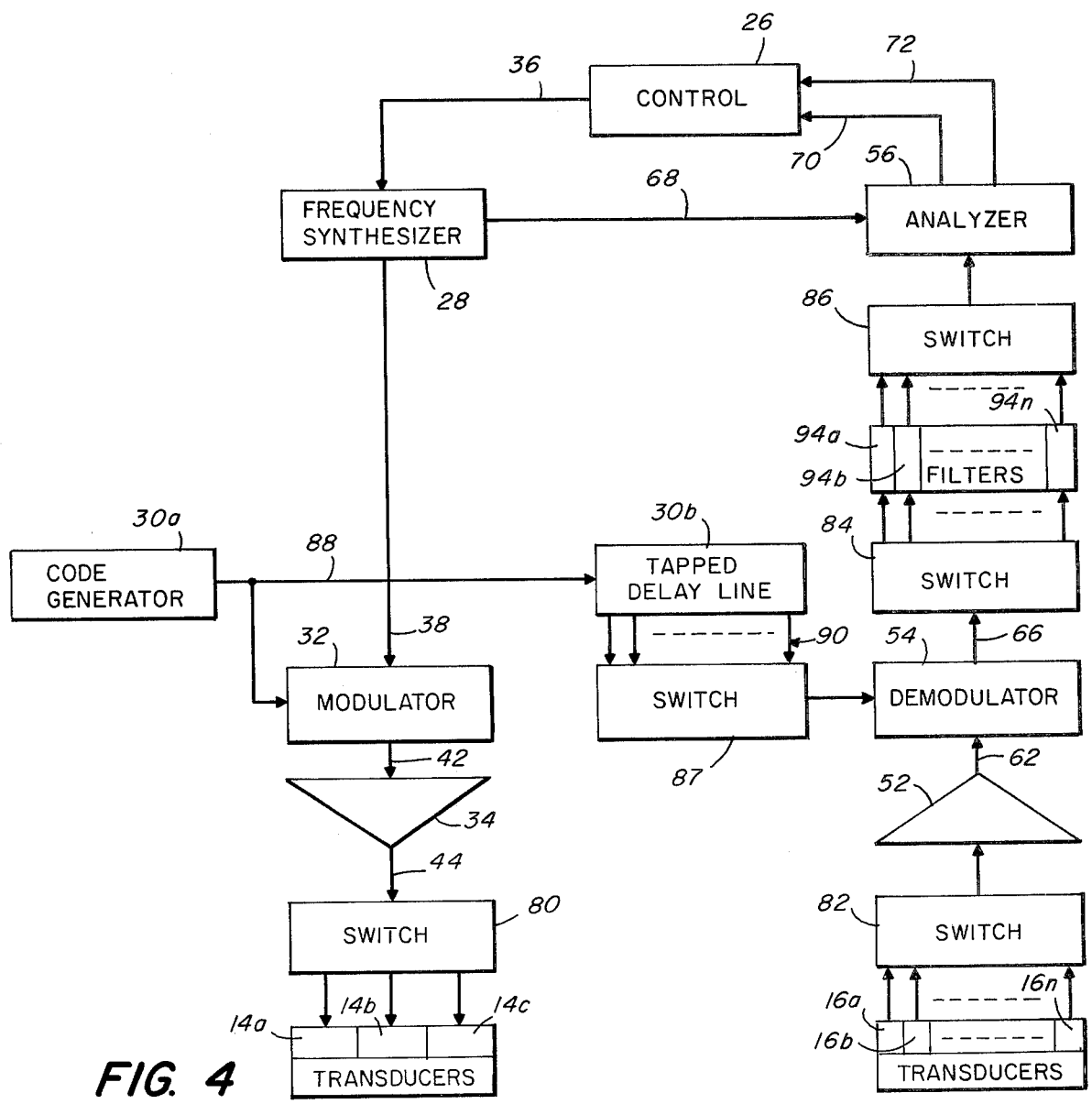
FIG. 4 is a schematic block diagram of a second particular embodiment of the invention employing plural transmitting transducers and receiving transducers.

Referring to FIG. 4, in the second particular embodiment of the invention, the control element 26 controls not only the frequency output of the frequency synthesizer 28 and the delay of code generation element 30, but further controls switching elements 80, 82, 84, 86 and 87 (by connections not shown).

The transmitter 10 in the second particular embodiment is modelled after the transmitter of FIG. 2. The control element 26 directs the output of the demodulator 32 and amplifier 34, through the switching element 80, to one of three different transmitting transducers 14a, 14b, 14c which are positioned relative to the solid at locations to illuminate the volume of interest of the solid. In this embodiment the code generation element of FIG. 2 is separated into a code generation section 30a having a code output over line 88 and a tapped digital delay line 30b having plural outputs over lines 90 to switch element 87.

Similarly, the receiver structure is modeled after that which was employed in FIG. 2. One selected receiver transducer 16a, 16b, 16c, . . . , is connected to amplifier 52 through the switching element 82. The amplifier 52 provides the received transducer signal to demodulator 54 and the output of the demodulator 54, in this particular embodiment, is passed through a selected narrow band crystal filter 94a, 94b, . . . , corresponding to the corresponding interrogation frequency from the frequency synthesizer 28. Switching elements 84 and 86 are operated synchronously to select the correct crystal filter. The output of the selected crystal filter is applied, through switching element 86, to the analyzing element 56 which provides the required phase and magnitude signals for later processing over lines 70, 72.

Thus, for each selected pair of transmitting and receiving transducers, the control element cycles the system through the selected frequencies and delays to provide the necessary data for later analysis and discriminant computations.

Figure 5:
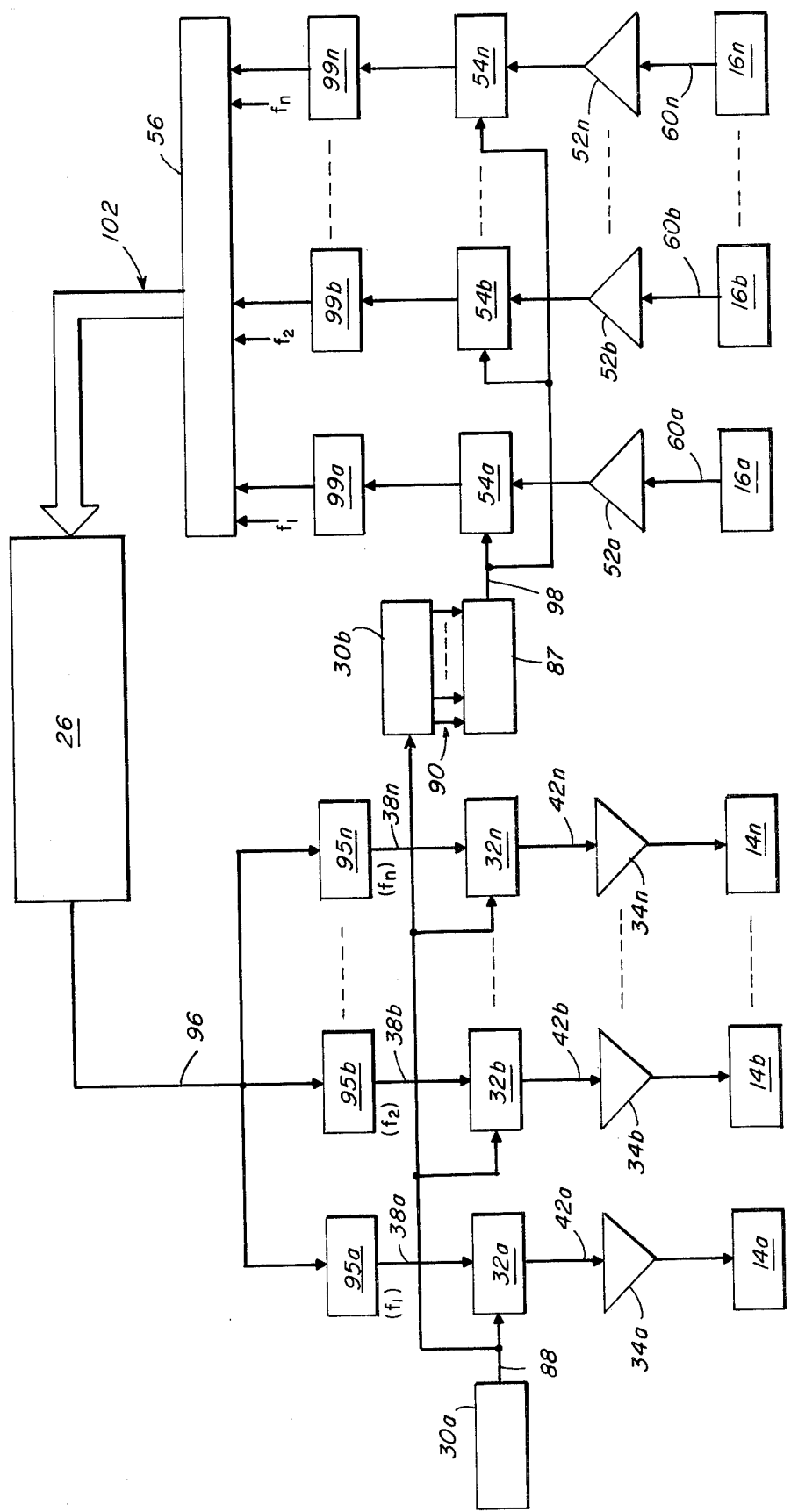
FIG. 5 is a schematic block diagram of a third particular embodiment of the invention wherein plural transmitting transducers simultaneously operate at plural interrogation frequencies.

Referring now to FIG. 5, in the third particular embodiment of the invention, the plural transmitting transducers are excited simultaneously, each with a generally different discrete frequency and the plural receiving transducers are simultaneously operative for receiving returning signals reflected from the solid being examined and to provide, through separate parallel signal processing paths, phase and amplitude data to the control element. Referring first to the transmitter portion of the circuit of the configuration of FIG. 5, the control element 26 provides to each of a plurality of frequency synthesizers 95a, 95b, . . . , data information over lines 96 to provide over output lines 38a, 38b, . . . , a plurality of different discrete sinusoidal frequencies $f_1$, $f_2$, . . . .

These sinusoidal signals are applied to separate modulators 32a, 32b, 32c, . . . , all of which are of the double balanced mixer circuit configuration. The modulators receive the code generation output over lines 88 and provide the respective phase modulated outputs over lines 42a, 42b, . . . , to amplifiers 34a, 34b, . . . . The outputs of the amplifiers are applied respectively to separate transmitter transducing elements 14a, 14b, . . . , for interrogation and examination of the sample being studied.

At the receiver, independently positioned receiving transducers 16a, 16b, . . . , provide over lines 60a, 60b, . . . , to amplifiers 52a, 52b, . . . , the respective reflected received signals. In general, each of the received signals provided by receiving transducers 16 contains reflections not only from a transmitting transducer of interest, but also reflections and noise from the other simultaneously operating transmitting transducers.

The outputs of amplifiers 52a, 52b, . . . , are applied to respective demodulators 54a, 54b, . . . . Demodulators 54 each receive over a line 98, a delayed replica of the pseudo-random code word for range gating the reflected received signals as described previously. The output of each modulator will therefore include a plurality of spectral frequencies corresponding not only to the desired frequency of interest, $f_i$, but also to the interfering or noise waveforms. As a result, the modulator outputs are connected to narrow band crystal filters 99 (for example 1 khz bandpass) to provide only the frequency of interest $f_i$. It is again particularly important to note that the code generation element code word length, $T_w$, must be chosen short enough so that it will not exceed the capability of crystal filters 100. Thus, if the code word length is made too great, the output of the demodulator may include spectral lines so close to one another (remember that the spacing of spectral lines equals $1/T_w$) that more than one spectral line will pass through a crystal filter thereby providing an erroneous signal output. However, for word lengths in the range of 500–2000 bits, the spectral spacing is acceptable for use with crystal bandpass filters.

The outputs of the crystal filters are applied to the network analyzer 56 which may be one or more of the Hewlett-Packard network analyzers. The analyzer 56 provides over lines 102, to the control element, the phase and signal magnitude of each of the input signals from the crystal filters. There is thus provided a parallel processing system which significantly reduces the examination time.

Other embodiments of the invention, including additions, subtractions, deletions, and other modifications of the disclosed particular embodiments will be obvious to those skilled in the art and are within the scope of the following claims.

What is claimed is:

1. An apparatus for examining the structure of a solid comprising
    transducer means responsive to electrical input signals for directing an interrogation signal toward the solid and for converting returning interrogation signals from the solid into received electrical signals,
    transmitter source means for providing said electrical input signals, said source comprising
        a code generating means for providing a repeating coded electrical signal output,
        frequency selection and generating means for generating electrical continuous wave signals according to a time sequence of selected discrete frequencies, and
        at least one modulation means for modulating said continuous wave signals with said coded electrical signal output for producing said electrical input signals for said transducer means, and
    receiver means responsive to said received electrical signals for demodulating and range gating said received signals for repeatedly providing electrical output data signals corresponding to selected sequential portions of the received signals relative to the continuous wave signal.

2. The apparatus of claim 1 wherein said receiver means comprises
    at least one demodulation means responsive to a delayed electrical coded signal output and to said received electrical signals for demodulating said received electrical signals and for providing a demodulated received signal, and
    at least one means associated with and responsive to each said demodulated received signal and to a continuous wave reference signal, said reference signal having the same instantaneous frequency as said corresponding continuous wave signal and a selected phase relationship to said corresponding continuous wave signal for generating said electrical output data signals.

3. The apparatus of claim 2 wherein said data signals correspond to the phase and magnitude of the returning interrogation signal relative to said interrogation signal.

4. The apparatus of claim 2 further comprising
    delay means associated with said code generating means for providing said delayed coded signal output at one of a plurality of selected delays.

5. The apparatus of claim 4 further comprising a sequencing control means for controlling the time sequence of said electrical continuous wave signals and for repeatedly varying the time delay of said delay means.

6. The apparatus of claim 2 wherein
    each modulation means comprises means for phase modulating said continuous wave signal according to said coded signal output.

7. The apparatus of claim 6 wherein
    each modulation means and demodulation means comprises a double balanced mixer.

8. The apparatus of claim 1 wherein said code generating means repeatedly generates a pseudo-random code word.

9. The apparatus of claim 2 further comprising
    transducer means having plural transmitting source transducers and plural receiving transducers,
    said source means further comprising
        means for simultaneously generating a plurality of continuous wave signals at selected discrete frequencies,
        separate modulation means associated with each continuous wave signal for modulating a said respective continuous wave signal with a selected coded signal, and
        means for applying said modulated signal outputs to separate ones of said source transducers, and
    said receiving means further comprising
        separate demodulator means responsive to said delayed coded signals for simultaneously demodulating the outputs of said respective receiver transducers, means for filtering said demodulated outputs for providing a plurality of filtered output signals corresponding respectively to said plural continuous wave signals, and means associated with each filtered signal and responsive to a corresponding continuous wave reference signal for generating corresponding output data signals representing at least one of said magnitude and phase of said filtered signal.

10. The apparatus of claim 9 wherein said modulation means comprises means for phase modulating said continuous wave signals in response to said coded signals, and said code generating means comprises means for generating a pseudo-random code of selected length.

11. An apparatus for examining the structure of a solid comprising transmitting means for repeatedly directing a phase modulated, discrete frequency interrogation signal at said solid, said interrogation signal comprising a plurality of time sequential modulated component signals, each component signal being associated with a different discrete frequency, and said modulating signal corresponding to a repeatedly generated pseudo-random code, and receiver means responsive to returning interrogation signals and to said modulating signal repeatedly delayed in accordance with a predetermined sequence of time durations, for generating data signals sequentially representing at least one parameter of said return signal at sequentially selected cells within said solid.

12. The apparatus of claim 11 wherein said parameters comprise the phase and magnitude of the return signals.

13. A method for analyzing the structure of a solid comprising the steps of directing interrogation signal energy toward said solid at each of a plurality of interrogation frequencies, said interrogation signal comprising a plurality of different, discrete frequency, continuous wave signals, each modulated by a repeating code signal, receiving returning interrogation signals from said solid, and providing, from said received returning signals, data output signals for each discrete frequency representing at least one parameter of said returning signals as a function of transit time.

14. The method of claim 13 wherein said parameters of said signal comprise the phase and the magnitude of the returning signal at a said discrete frequency relative to the interrogation signal at said frequency.

15. The method of claim 13 further comprising the steps of generating at least one discriminant value based upon said data output signals, and estimating the structure of said solid based upon said at least one discriminant value.

16. The method of claim 15 wherein said generating step comprises generating the spatial gradient of the phase of the returning signals as a function of frequency.

17. The method of claim 15 wherein said generating step comprises generating the spatial gradient of the magnitude of the returning signals as a function of frequency.

18. The method of claim 15 wherein said generating step comprises generating the absolute phase of the returning signals within a selected examination cell of the solid as a function of frequency.

19. The method of claim 15 wherein said generating step comprises generating the rate of change of phase of the returning signals within a selected examination cell of the solid as a function of frequency.

20. The method of claim 15 wherein said generating step comprises generating the magnitude of the returning signals within a selected examination cell of the solid as a function of frequency.

21. The method of claim 15 wherein said generating step comprises generating the rate of change of the magnitude of said returning signals within a selected examination cell of the solid as a function of frequency.

22. The method of claim 15 wherein said generating step comprises generating the integral, over the applied frequency range, of the returning signal magnitude for examination cells of the solid.

23. The method of claim 13 wherein said interrogation frequencies are selected to permit interpolation between data corresponding to adjacent frequencies, and further comprising the step of interpolating the phase and signal magnitude values for a selected examination cell of the solid between adjacent interrogation signal frequencies.

24. The method of claim 13 further comprising the steps of simultaneously directing interrogation energy at each of a plurality of frequencies into said solid, and simultaneously receiving said returning signals at each of a plurality of receiving transducers.

25. The method of claim 13 further comprising the steps of generating a pseudo-random code for said code signal, time gate demodulating said returning signals using a delayed replica of said pseudo-random code, and selectively varying the time delay of said replica.

26. The method of claim 25 further comprising the step of modulating said continuous wave signals using phase modulation.

27. The method of claim 13 further comprising the step of sequentially generating said discrete frequency, continuous wave signals.

28. The method of claim 27 further comprising the step of switchably connecting in a predetermined pattern, receiving transducers to selected receiver components to process the returning signals corresponding to said different discrete frequencies.

* * * * *